United States Patent
Camacho Perez et al.

(10) Patent No.: US 10,298,282 B2
(45) Date of Patent: May 21, 2019

(54) MULTI-MODAL SENSING WEARABLE DEVICE FOR PHYSIOLOGICAL CONTEXT MEASUREMENT

(71) Applicant: Intel Corporation, Santa Clara, CA (US)

(72) Inventors: Jose Rodrigo Camacho Perez, Guadalajara Jalisco (MX); Alejandro Ibarra Von Borstel, Tlajomulco (MX); Hector Alfonso Cordourier Maruri, Guadalajara (MX); Julio Cesar Zamora Esquivel, Zapopan (MX); Paulo Lopez Meyer, Zapopan (MX)

(73) Assignee: Intel Corporation, Santa Clara, CA (US)

( * ) Notice: Subject to any disclaimer, the term of this patent is extended or adjusted under 35 U.S.C. 154(b) by 121 days.

(21) Appl. No.: 15/184,993

(22) Filed: Jun. 16, 2016

(65) Prior Publication Data

US 2017/0366213 A1    Dec. 21, 2017

(51) Int. Cl.
*A61B 5/00*    (2006.01)
*H04B 1/3827*    (2015.01)
(Continued)

(52) U.S. Cl.
CPC ........... *H04B 1/385* (2013.01); *A61B 5/0008* (2013.01); *A61B 5/02055* (2013.01);
(Continued)

(58) Field of Classification Search
CPC ... A61B 5/0205; A61B 5/0476; A61B 5/0402; G16H 50/20; H04B 1/385
See application file for complete search history.

(56) References Cited

U.S. PATENT DOCUMENTS 1,823,228 A    9/1931    Apfel
1,897,833 A    2/1933    Benway
(Continued)

FOREIGN PATENT DOCUMENTS

CN    101742387 A    6/2010
JP    D3121603 A    5/1991
(Continued)

OTHER PUBLICATIONS

U.S. Appl. No. 14/749,960, entitled "Wearable Device With Gesture Recognition Mechanism," filed Jun. 25, 2015.
(Continued)

*Primary Examiner* — Michael J D Abreu
(74) *Attorney, Agent, or Firm* — Schwabe, Williamson & Wyatt, P.C.

(57) ABSTRACT

Embodiments of the present disclosure provide techniques and configurations for an apparatus for a user's physiological context measurements. In one instance, the apparatus may include a processing block and first and second piezoelectric sensors coupled with the processing block. The first and second sensors may include respectively first and second electrodes to provide contact with a user's body in response to mounting of the apparatus on the user's body. The processing block may comprise a multi-modal sensing system configured to perform measurements of a user's physiological context during the contact of the user's body with the first and second electrodes, based at least in part on a voltage signal generated by the user's body and provided to the processing block via the first and second electrodes. Other embodiments may be described and/or claimed.

15 Claims, 10 Drawing Sheets

(51) Int. Cl.

| | |
|---|---|
| *A61B 5/0476* | (2006.01) |
| *A61B 5/0402* | (2006.01) |
| *A61B 5/0488* | (2006.01) |
| *H04W 4/70* | (2018.01) |
| *A61B 5/0205* | (2006.01) |
| *A61B 5/021* | (2006.01) |
| *A61B 5/024* | (2006.01) |
| *A61B 5/053* | (2006.01) |
| *A61B 5/08* | (2006.01) |
| *A61B 5/11* | (2006.01) |

(52) U.S. Cl.
CPC .......... *A61B 5/0402* (2013.01); *A61B 5/0476* (2013.01); *A61B 5/0488* (2013.01); *A61B 5/6802* (2013.01); *H04W 4/70* (2018.02); *A61B 5/0075* (2013.01); *A61B 5/021* (2013.01); *A61B 5/02416* (2013.01); *A61B 5/0531* (2013.01); *A61B 5/08* (2013.01); *A61B 5/1112* (2013.01); *A61B 5/681* (2013.01)

(56) References Cited

U.S. PATENT DOCUMENTS

| | | | |
|---|---|---|---|
| 1,935,923 | A | 11/1933 | Thoke |
| 1,940,553 | A | 12/1933 | Hugo |
| 2,045,404 | A | 6/1936 | Christ |
| 2,062,373 | A | 12/1936 | Christ |
| 2,451,317 | A | 10/1948 | Blair et al. |
| 2,613,282 | A | 10/1952 | Scaife |
| 2,813,933 | A | 11/1957 | Williams et al. |
| 2,850,584 | A | 9/1958 | Smith |
| 3,183,312 | A | 5/1965 | Jechiel et al. |
| 4,520,238 | A | 5/1985 | Ikeda |
| 7,148,879 | B2 | 12/2006 | Amento et al. |
| 7,555,136 | B2 | 6/2009 | Wang |
| 7,580,540 | B2 | 8/2009 | Zurek et al. |
| 8,856,875 | B2 | 10/2014 | Aditya |
| 9,002,020 | B1 | 4/2015 | Kim et al. |
| 9,094,749 | B2 | 7/2015 | Xie et al. |
| 2003/0091134 | A1 | 5/2003 | Chi et al. |
| 2003/0228023 | A1 | 12/2003 | Burnett et al. |
| 2005/0286734 | A1 | 12/2005 | Wang |
| 2006/0140422 | A1 | 6/2006 | Zurek et al. |
| 2007/0064535 | A1 | 3/2007 | Burnstad |
| 2007/0167850 | A1* | 7/2007 | Russell ................ A61B 5/0205 600/513 |
| 2010/0110368 | A1 | 5/2010 | Chaum |
| 2010/0331649 | A1 | 12/2010 | Chou |
| 2011/0224481 | A1 | 9/2011 | Lee |
| 2012/0007713 | A1 | 1/2012 | Nasiri et al. |
| 2012/0256821 | A1 | 10/2012 | Olsson et al. |
| 2012/0282976 | A1 | 11/2012 | Suhami |
| 2012/0306745 | A1 | 12/2012 | Moore et al. |
| 2013/0022220 | A1 | 1/2013 | Dong |
| 2013/0159705 | A1 | 6/2013 | Leedom, Jr. |
| 2013/0242262 | A1 | 9/2013 | Lewis |
| 2014/0029762 | A1 | 1/2014 | Xie |
| 2014/0064536 | A1 | 3/2014 | Kim et al. |
| 2014/0112503 | A1 | 4/2014 | Hebenstreit |
| 2014/0161287 | A1 | 6/2014 | Liu et al. |
| 2014/0176439 | A1 | 6/2014 | Keller et al. |
| 2014/0275852 | A1 | 9/2014 | Hong et al. |
| 2014/0378113 | A1 | 12/2014 | Song et al. |
| 2015/0031964 | A1* | 1/2015 | Bly ..................... A61B 5/7465 600/301 |
| 2015/0074797 | A1 | 3/2015 | Choi et al. |
| 2015/0135310 | A1 | 5/2015 | Lee |
| 2015/0160622 | A1 | 6/2015 | Kim et al. |
| 2015/0185838 | A1 | 7/2015 | Camacho-Perez et al. |
| 2015/0289820 | A1 | 10/2015 | Miller et al. |
| 2016/0070245 | A1 | 3/2016 | Lee et al. |
| 2016/0091980 | A1 | 3/2016 | Baranski et al. |
| 2016/0246368 | A1 | 8/2016 | Camacho-Perez et al. |
| 2016/0282945 | A1 | 9/2016 | Ochoa |
| 2016/0284135 | A1 | 9/2016 | Zamhi |
| 2016/0378193 | A1 | 12/2016 | Rodrigo |
| 2017/0078788 | A1 | 3/2017 | Meyer |
| 2017/0090583 | A1 | 3/2017 | Zamora Esquivel et al. |

FOREIGN PATENT DOCUMENTS

| | | | |
|---|---|---|---|
| KR | 10-2011-0068579 | A | 6/2011 |
| KR | 10-2012-0080852 | A | 7/2012 |
| KR | 10-2013-0035290 | A | 4/2013 |
| WO | 2011/094366 | A1 | 4/2011 |
| WO | 2015123771 | A1 | 8/2015 |

OTHER PUBLICATIONS

U.S. Appl. No. 15/078,746, entitled "User's Physiological Context Measurement Method and Apparatus," filed Mar. 23, 2016.

U.S. Appl. No. 14/855,746, entitled Techniques for Gesture Recognition Using Photoplethysmographic (PPMG) Sensor and Low-Power Wearable Gesture Recognition Device Using the Same, filed Sep. 16, 2015.

U.S. Appl. No. 14/854,927, entitled "System for Voice Capture via Nasal Vibration Sensing," Sep. 15, 2015.

U.S. Appl. No. 14/965,095, entitled "System for Sound Capture and Generation via Nasal Vibration," filed Dec. 10, 2015.

International Search Report issued in PCT Application No. PCT/US2016/017413, dated Jul. 6, 2016, 15 pages.

Amento, et al."The Sound of One Hand: A Wrist-mounted Bioacoustic Fingertip Gesture Interface, " Short Talk: It's All About Sound, CHI 2002, Apr. 20-25, 2002, Minneapolis, Minnesota, USA, pp. 724-725, retrieved on Mar. 15, 2018 from URL <<http://citeseerx.ist.psu.edu/viewdoc/download?doi=10.1.1.10.2398&rep=rep1&type=pdf>>.

Non-Final Office Action dated Nov. 16, 2016 issued in related U.S. Appl. No. 14/749,960, 16 pages.

Office Action dated Nov. 16, 2016 issued in related U.S. Appl. No. 14/749,960, 18 pages.

Tamura,Toshiyo, et al.; "Wearable Photoplethysmographic Sensors—Past and Present", Electronics, No. 3, 2014, pp. 282-302, DOI:10.3390/electronics3020282.

H. Han, J. Kim, "Artifacts in wearable photoplethysmographs during daily life motions and their reduction with least mean square based active noise cancellation method", Computers in biology and medicine, 42(4), Apr. 2012, pp. 387-393, Abstract only.

K.F. Teng, Y.T. Zhang, "The effect of contacting force on photoplethysmographic signals", Physiological Measurement, No. 25, Aug. 11, 2004, pp. 1323-1335, Abstract only.

Park, C.R. Farrar, A. C. Rutherford, A.N. Robertson, "Piezo-Sensor Self-Diagnostics Using Electrical Impedance measurements", Los Alamos National Laboratory, Technical Report LA-UR-04, Oct. 24-27, 2004, 17 pages.

Myo Armband, hllps://www.thalmic.com/myo, downloaded Mar. 22, 2017, 5 pages.

Chianura, A., et al.: "Electrooptical muscle contraction sensor", Medical & biological engineering & computing, 48(7), pp. 731-734, Jul. 2010, 12 pages.

Raghavendra, J.: "Optomyography: detection of muscle surface displacement using reflective photo resistor", MSc. Thesis, KTH Technology and Health, Stockholm, Aug. 2014, pp. 1-31.

Cheng, E.Y., et al: "Forehead pulse oximetry compared with finger pulse oximetry and arterial blood gas measurement", Journal of Clinical Monitoring, Jul. 4, 1988, vol. 4, Issue 3, pp. 223-226, Abstract only.

Barry, D.T., et al: "Acoustic myography as a control signal for an externally powered prosthesis", Archives of Physical Medicine and Rehabilitation, vol. 67, No. 4, Apr. 1986, pp. 267-269, Abstract only.

Overly, T.G., et al: "Piezoelectric active-sensor diagnostics and validation using instantaneous baseline data", IEEE Sensors Journal, vol. 9, No. 11, Nov. 2009, pp. 1414-1421, Abstract only.

Lim, J. M., et al: "Recognizing hand gestures using wrist shapes". In Consumer Electronics {ICCE), 2010 Digest of Technical Papers International Conference, IEEE, Jan. 2010, pp. 197-198, Abstract only.

(56) References Cited

OTHER PUBLICATIONS

International Search Report issued in PCT Application No. PCT/US2016/047206, dated Oct. 27, 2016, 12 pages.
Alian, A. A., et al: "Photoplethysmography." Best Practice & Research Clinical Anaesthesiology, 28(4), Dec. J014, pp. 395-406, Abstract only.
Mason, W.P., et al.: "Methods for Measuring Piezoelectric, Elastic, and Dielectric Coefficients of Crystals and : eramics", Proceedings of the IRE.vol. 42, Jun. 6, 1954, 1 page, Abstract only.
Harrison, Chris, et al.: "Skinput: Appropriating the Body as an Input Surface", http://www.chrisharrison.net/index.php/Research/Skinput, downloaded Mar. 22, 2017, 10 pages.
Final Office Action issued in U.S. Appl. No. 14/965,095, dated May 2, 2017, 21 pages.
U.S. Office Action issued in U.S. Appl. No. 14/965,095, dated Oct. 21, 2016.
International Search Report and Written Opinion issued in PCT Application No. PCT/US2016/047089, dated Oct. 26, 2016.
Hakansson et al., "Resonance Frequencies of the Human Skull in Vivo Department of Applied Electronics", Chalmers University of Technology, Gothenburg, Sweden, Nov. 12, 1993.
Carter, et al., "Estimation of the Magnitude-Squared Coherence Function via Overlapped Fast Fourier Transform Processing", IEEE Transactions on Audio and Electroacoustics, vol. AU-21, No. 4, Aug. 1973.
Welch, "The Use of Fast Fourier Transform for the Estimation of Power Spectra: A Method Based on Time Averaging Over Short, Modified Periodograms", IEEE Transactions on Audio and Electroacoustics, vol. AU-15, No. 2, Jun. 1967.
Interational Search Report and Written Opinion issued in PCT Application No. PCT/US2016/061420, dated Jan. 18, 2017, 15 pages.
Piezoelectric Sound Components, muRata catalogue, May 2014.
U.S. Office Action issued in U.S. Appl. No. 14/854,927, dated Sep. 1, 2016.

\* cited by examiner

MULTI-MODAL SENSING WEARABLE DEVICE FOR PHYSIOLOGICAL CONTEXT MEASUREMENT

FIELD

Embodiments of the present disclosure generally relate to the field of wearable devices, and more particularly, to wearable devices also configured to measure a user's physiological context using multi-modal sensing.

BACKGROUND

Portable or wearable devices continue to increase in popularity, and feature increasingly sophisticated functionality, including wireless capabilities. Some of the devices may be used to monitor human body events like physical activity, gestures, speech, health, emotional state, etc. These events may be manifested by various bio-signals like electric (from skin conductivity and brain or muscle activity, etc.), mechanical (from tissue displacement or voice, etc.), temperature, and optical (from tissue and blood reflectance). Accordingly, in order to monitor such events, a device may be configured to measure a user's physiological context, such as respiration cycle, heart rate, temperature, or the like.

The performance of these applications may be related to the amount of information that may be obtained from the bio-signals. For instance, enhanced body activity tracking may be obtained if activity is sensed concurrently not only through inertial measurement units (IMUs) but also through electrocardiograms (ECG) and mechanomyograms (MMG). Similarly, gestures detection may be enhanced by concurrent use of IMUs, MMGs, photoplethysmograms (PPMG) and electromyograms (EMG). Emotional state may be monitored, for example, through concurrent electroencephalograms (EEG), functional near-infrared (fNIR) spectroscopy, PPMG (for pulse monitoring) and MMG (for respiration monitoring). Sensing multiple types of bio-signals may require using multi-modal bio-sensors. However, typical bio-sensors may transduce only one type of bio-signals.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Figure 1:
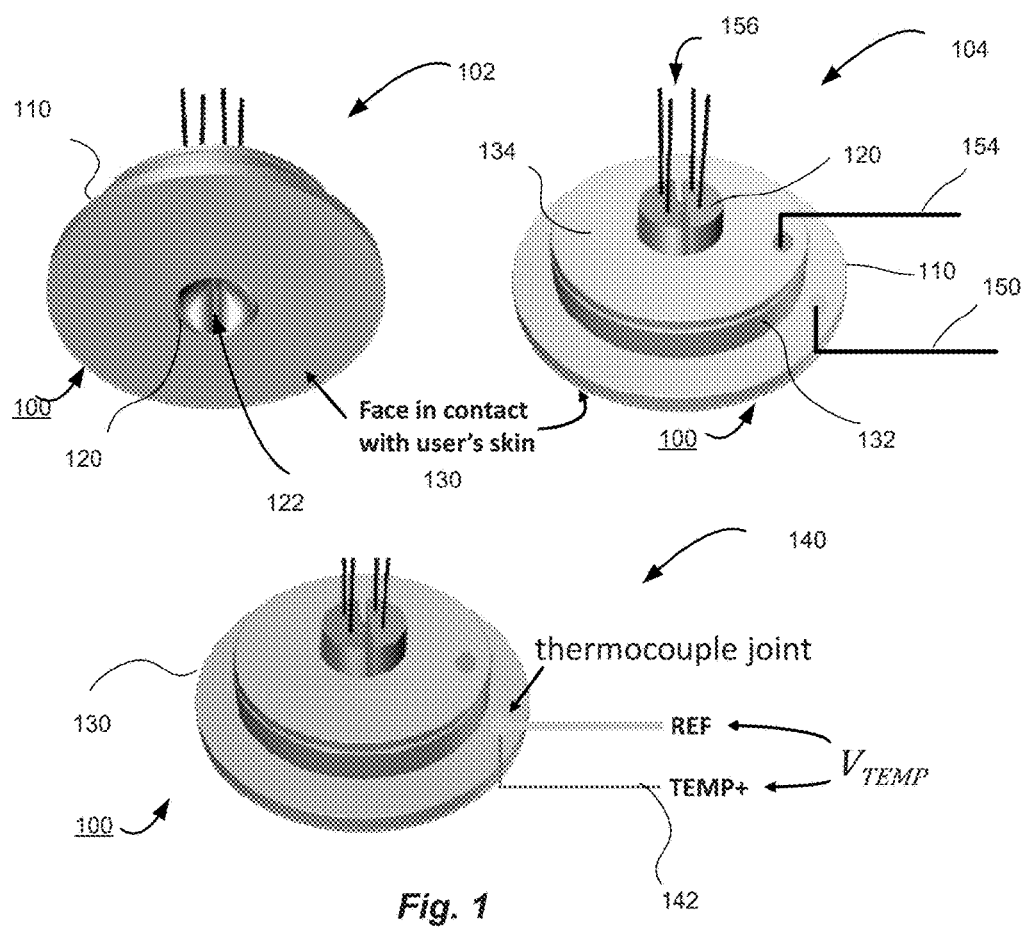
FIG. 1 is a diagram illustrating perspective views of an example integrated sensor configured to provide readings of a user's physiological context, in accordance with some embodiments.

Embodiments of the present disclosure include techniques and configurations for an apparatus and method for a user's physiological context measurements using multi-modal sensing. In some embodiments, the apparatus may include a processing block (comprising a multi-modal sensing system) and a sensor array coupled with the processing block. The sensor array may include a first sensor, having at least a first electrode to provide a first contact with a user's body in response to mounting of the apparatus on the user's body. The first electrode may be coupled with the processing block, to facilitate a provision of a first signal to be generated by the first sensor to the processing block in response to the first contact. The sensor array may further include a second sensor, having at least a second electrode to provide a second contact with the user's body in response to mounting of the apparatus on the user's body. The second electrode may be coupled with the processing block, to facilitate a provision of a second signal to be generated by the second sensor to the processing block in response to the second contact.

The processing block may comprise a multi-modal sensing system to perform measurements of a user's physiological context based at least in part on a voltage signal to be generated by the user's body and provided by the first and second electrodes in response to the first and second contacts of the user's body with the first and second sensors, and further based on the first and second signals provided by the first and second sensors.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), (A) or (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment" or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

FIG. 1 is a diagram illustrating perspective views of an example integrated sensor configured to provide readings of a user's physiological context, in accordance with some embodiments. The integrated sensor 100 may include different sensing components and may be used in a sensor array embedded in a wearable device to provide sensing of different types of the user's physiological context, such as voltage generated by the user's body, user's temperature, breathing and cardiac cycles, and the like. The sensor array may include one or more (or two or more) integrated sensors 100 embedded in a wearable device, to provide close proximity or contact with a user's body. For example, the integrated sensor 100 may be disposed on a watch opposite the face, thus providing close proximity to human tissue. As described below, other wearable devices may include the integrated sensor, and this disclosure is not limited in this regard.

More specifically, FIG. 1 provides perspective views 102 and 104 of the integrated sensor. As shown, the sensor 100 may include at least a piezoelectric (PZE) sensor component 110 and a photoplethysmography (PPMG) sensor component 120 in a single housing (not shown). The PZE sensor component 110 may detect mechanical vibrations (e.g., associated with the user's body) and output a proportional electrical signal. The PPMG sensor component 120 may comprise an infrared (IR) light emitting diode (LED) and an IR sensor or photodetector (PD). The PPMG sensor component 120 may optically detect changes in the blood flow volume and tissue displacement through emitting light and detecting changes in the light reflected back, and may output an electrical signal based on those detected changes, in order to measure breathing or cardiac cycles, for example.

The PPMG and PZE components may provide respective sensor output signals that may be used individually, or in concert, to perform user's physiological context measurements. The measurements may be used for different purposes, such as monitoring of the user's health and activities. In one example, the physiological context measurements may be used for determining different tasks associated with the user's activity, such as gesture recognition, for example.

In the illustrative embodiment of FIG. 1, the PZE sensor component 110 may include one or more openings 122 configured to receive at least a portion of one or more PPMG sensor components 120. The openings 122 may be referred to as a PPMG receptacle. While examples provided herein include a rounded PZE component 110, other shapes and configurations are also within the scope of this disclosure. As shown, the PZE component 110 may include a first (bottom) electrode 130, a second (top) electrode 134, and a sensing layer 132 comprising a piezoelectric material. The sensing layer 132 may be sandwiched between the first and second electrodes 130 and 134.

The first and second electrodes 130 and 134 may comprise conductive material, such as metal, for example. In the embodiments on views 102, 104, the first and second electrodes 130 and 134 may have a disk-shaped form. The first (bottom) electrode 130 may provide a contact with a user's skin in response to mounting of a wearable apparatus including the sensor 100 on the user's body.

As shown in view 104, the electrodes 130 and 134 of the PZE sensor component 110 may be coupled with a processing block of a wearable device (not shown) via contacts (e.g., wires) 150, 154 respectively. As further shown, the PPMG sensor component 120 may be coupled with the processing block via a contact array 156.

View 140 illustrates another embodiment of the sensor 100. In addition to components described in reference to views 102 and 104, the sensor 100 may further include a thermocouple 142. As shown, the thermocouple 142 may include two wires soldered together on the first electrode 130 (metal disk). In other configurations (not shown), the thermocouple 142 may include wires that may be soldered apart on the first electrode 130. One of the wires of thermocouple 142 may be the contact 150 shown in view 104. One of the wires of the thermocouple 142 may serve as a common ground for the sensor 100. The thermocouple may be in close contact with the user's body, and may provide for measurements of the user's temperature in addition to other measurements of the user's physiological context described above. Accordingly, the addition of a thermocouple to the sensor 100 may enable continuous body temperature monitoring.

Figure 2:
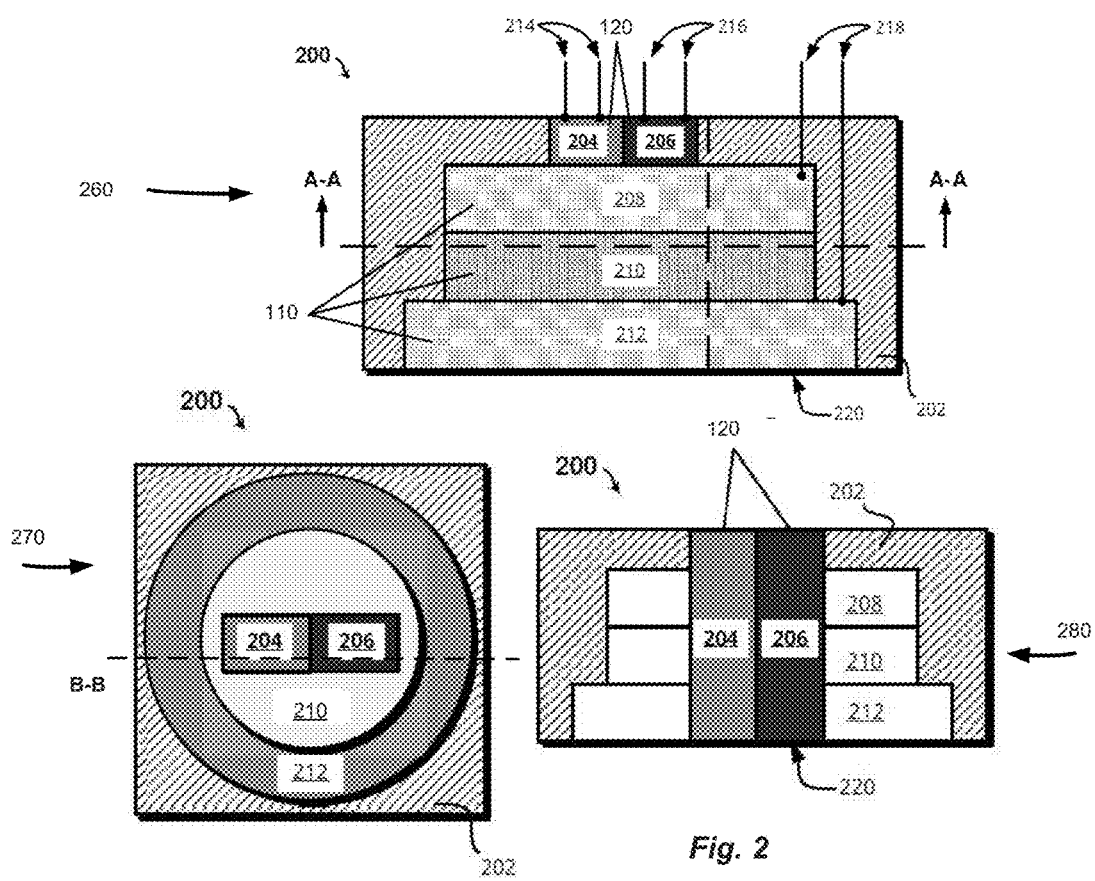
FIG. 2 is a schematic diagram illustrating different views of an example integrated sensor, in accordance with some embodiments.

FIG. 2 is a schematic diagram illustrating different views of an example integrated sensor provided in accordance with embodiments of the present disclosure. The integrated sensor 200 of FIG. 2 may comport with the embodiments of the sensor described in reference to FIG. 1. As shown in side view 260 of the sensor 200, the integrated sensor 200 may include a substrate 202, an IR LED 204, an IR sensor 206 or photodetector, a bottom (first) electrode 212 or conductor, a top (second) electrode 208 or conductor, a PZE slab 210 of PZE material, LED terminals 214, IR sensor terminals 216, and PZE sensor terminals 218. Components 208, 210, and 212 may comprise the PZE sensor component 110 of FIG. 1. Components 204 and 206 may comprise the PPMG sensor component 120 of FIG. 1.

The substrate 202 may comprise, for example, a non-conductive material such as glass, plastic, polycarbonate. In some cases, the non-conductive material includes acrylonitrile-butadine-styrene (ABS) or any of the polymeric encapsulant materials used for micro-electronic circuit packaging like epoxies, silicones, acrylics, polyimides, cyanate esters and amorphous polymers. The substrate may provide structural support for the sensor and a protective housing. The substrate 202 may provide support for the PZE sensor component 110 such that the bottom (second) electrode 212 may be in direct contact with the skin. To this end, the substrate 202 may include an opening at the base 220 allowing a bottom surface of the bottom electrode 212 to make contact with a user's skin.

The top and bottom electrodes 208 and 212, respectively, may comprise electrically conductive material such as, for example, copper, or other suitable metals. In some cases, the top and bottom electrodes 208 and 212 comprise a metal such as brass or gold that resists corrosion and is not particularly irritating to the user's skin. Alternatively, bottom electrode 212 may include a protective coating that resists corrosion and avoids allergic or otherwise unpleasant reaction with skin. This through-hole may be described as a PPMG sensor receptacle.

A cross-sectional view 270 of the integrated sensor 200 is shown taken along the line A-A of view 260. As shown, the top electrode 208 and bottom electrode 212 may include a generally circular or rounded shape and may also be generally concentric. In other embodiments, the electrodes 208 and 212, and the PZE material 208 may be of any shape, including regular (e.g., circular, rectangular, hexagonal, etc.), or irregular, including non-concentric.

A cross-sectional view 280 of the integrated sensor 200 is shown taken along the line B-B of view 270. As shown, the IR LED 204 and the IR sensor 206 may extend from a top of the hybrid sensor device 200 to the base 220. A through-hole formed in the top electrode 208, PZE slab 210 and the bottom electrode 212 is configured to receive the IR LED 204 and the IR sensor 206, and to allow the same to make direct contact or otherwise be in close proximity to a user's skin.

Figure 3:
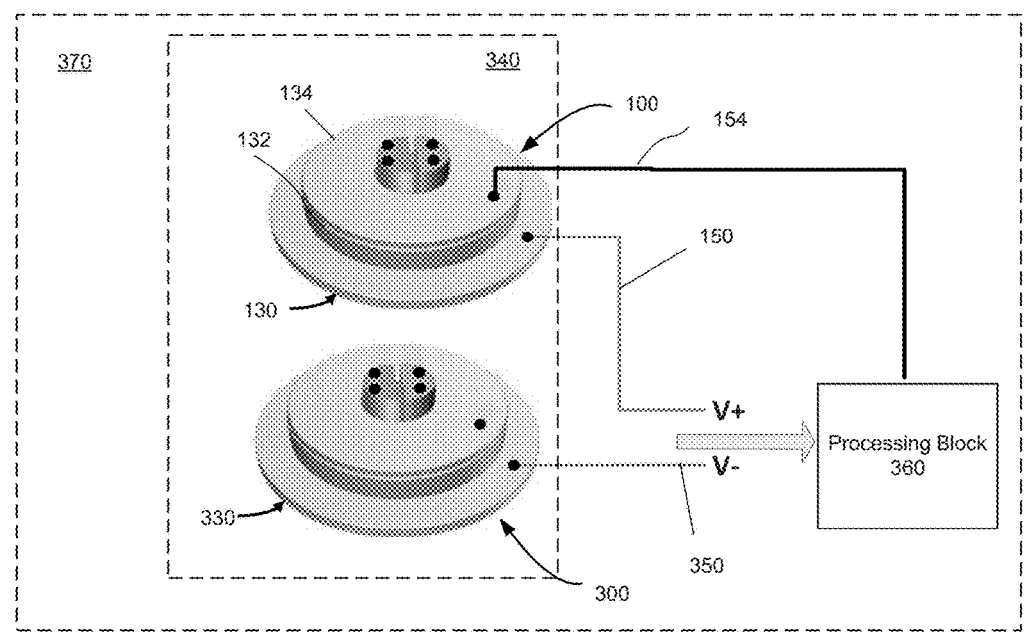
FIG. 3 is a diagram illustrating an example sensor array comprising two or more integrated sensors, in accordance with some embodiments.

FIG. 3 is a diagram illustrating an example sensor array comprising two or more integrated sensors, in accordance with some embodiments. The example sensor array may be used in a wearable device for multi-modal sensing of a user's physiological context, as will be described below in greater detail. For ease of understanding, the like components of FIGS. 1 and 3 are indicated by like numerals, and the diagram provides a simplified illustration of the example sensor array.

As shown in FIG. 3, the electrodes 130 and 134 of the PZE sensor component 110 of the sensor 100 may be coupled with a processing block 360 of a wearable device 370 via contacts 150, 154. The PZE sensor component 110 may generate a signal in response to the contact or close proximity of the bottom electrode 130 of the sensor 100 with the body of the user, in response to mounting the wearable device 370 to the user's body. Accordingly, electrodes 130 and 134 may provide readings of vibrations produced by the user's body and sensed by the sensing layer 132, via contacts 150, 154, to the processing block 360 of the wearable device 370.

If the sensor 100 may be electrically coupled with another identical or similar sensor 300, the respective bottom electrodes 130, 330 of these sensors may be used to sense or induce electric voltages. In other words, the bottom electrodes 130, 330 of the sensors 100, 300 may be used as a voltage probe: the voltage signal between the electrodes 130, 330 may comprise a difference between respective voltages on the electrodes 130 and 330 and may reflect, for example, the voltage generated by the user's body when the sensors 100, 300 are in contact or in close proximity to the user's body.

Accordingly, the sensors 100, 300 may be electrically coupled to form an array 340, which may be embedded in the wearable device 370. In the array 340, the bottom electrodes 130, 330 of the sensors 100, 300 may be used to sense voltages generated by the user's body in response to contact of the sensors 130, 330 with the user's body, in addition to their use as PZE electrodes for their respective PZE sensor components. As shown, one of the bottom electrodes (e.g., 330) and its respective contact (e.g., 350) may serve as reference voltage for another electrode and contact (130 and 150 respectively).

The examples of application of the array 340 in the wearable device 370 may include, but are not limited to, collecting electrocardiogram (ECG) data, electromyogram (EMG) data, or electroencephalogram (EEG) data as reflected by the voltage generated by the body of the user, in addition to collecting data provided by respective PZE sensor components and PPMG sensor components, as well as respective thermocouples of the sensors of the array. The ECG, EEG, and EMG data may be provided to the processing block 360 via contacts 150, 350 for processing as described below in greater detail. In summary, mechanical, optical, temperature, and voltage signals may be sensed substantially concurrently, using the wearable device 370 with the sensor array 340, thus providing a multi-modal sensing of the user's physiological context.

Further, the wearable device 370 may be configured to generate and induce voltage into the user's body via the electrodes 130, 330 of the sensors 100, 300, to perform further measurements of the user's physiological context or provide treatment. For example, inducing voltage may provide for measurement of skin conductance, in order to estimate the user's stress level. In another example, inducing voltage may provide for muscle stimulation to perform therapeutic treatment of the user, for example, to electrically stimulate the user's skin. In another example, inducing voltage may provide for skin and muscle stimulation for haptic interfaces, such as inducing a sensory feedback from the computer to the user. In another example, inducing voltage may provide for skin capacitance sensing for touch interfaces, such as to sense when and where the user may be touching objects or when and where an object may be touching the user's skin.

In a different application, inducing voltage may provide for inducing mechanical signals, for example, for ultrasound imaging. More specifically, a mechanical vibration signal may be induced via the piezoelectric sensor through contacts 150-154 and may be sensed back with a different sensor in the sensor array.

In still a different application, inducing voltage may provide for wireless intrabody communication, such as for transmission of electrical signals across the skin that may be read by another device a distance away from the user.

In yet another application, inducing voltage (e.g., through contacts 214 and 216 of FIG. 2) may be used to drive the LED of the PPMG sensor components of the sensors.

While two sensors 100 and 300 are shown in FIG. 3 as forming the example array 340, any number of sensors 100 equal to or greater than two may be used to form the array 340, in order to provide measurements of the user's physiological context.

Figure 4:
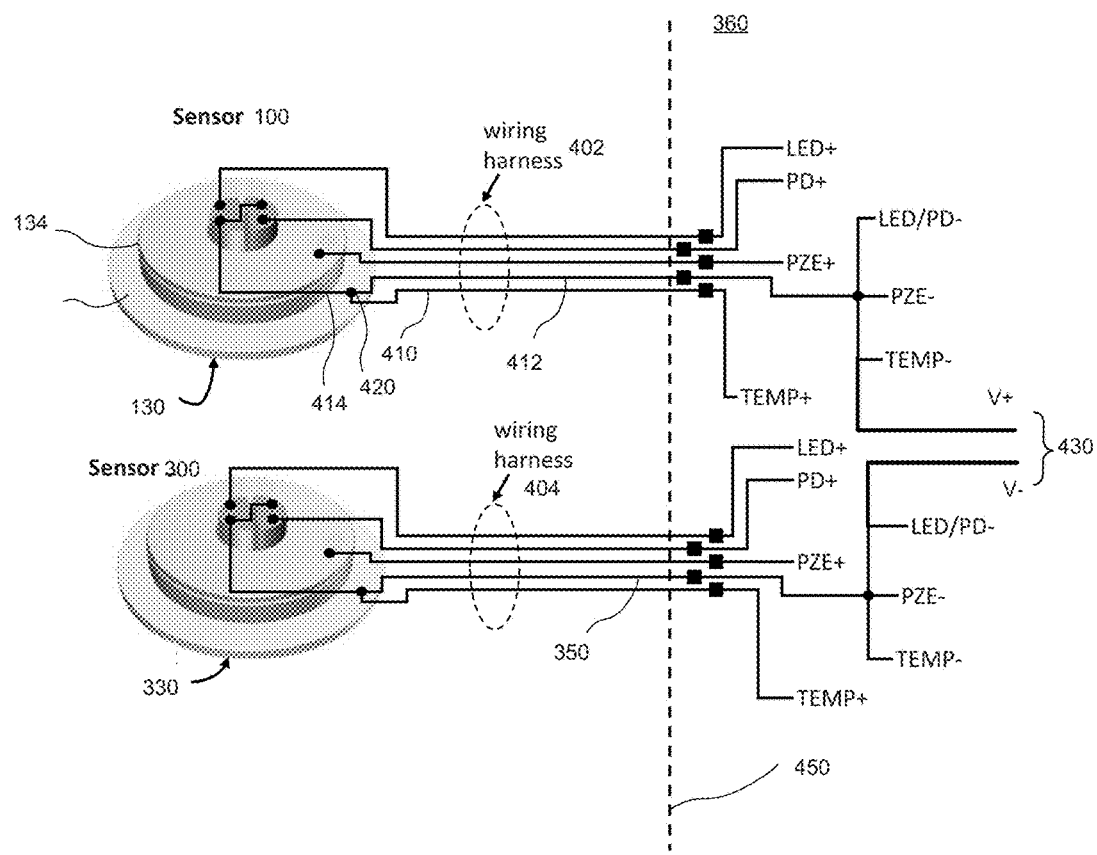
FIG. 4 is a schematic diagram illustrating an example coupling of the sensor array of FIG. 3 with a processing block of an apparatus, such as a wearable device, in accordance with some embodiments.

FIG. 4 is a schematic diagram illustrating an example coupling of the sensor array of FIG. 3 with a processing block of an apparatus, such as a wearable device, to provide multi-modal sensing of a user's physiological context, in accordance with some embodiments. For ease of understanding, the like components of FIGS. 1, 3, and 4 are indicated by like numerals.

The sensor 100 may be connected with the processing block 360 (disposed, e.g., on a printed circuit board (PCB) 450 marked by a dashed line), via wiring interconnection harness 402. Similarly, the sensor 300 may be connected with the processing block 360 via wiring interconnection harness 404. The interconnection of sensor 100 with the processing block 360 will now be described in detail.

As shown, the electrode 130 of the sensor 100 may be connected with the processing block 360 via contacts 410, 412 extending from a joint 420 disposed on the electrode 130. The contact 410 may comprise a thermocouple contact TEMP+. The contact 412 may comprise another thermocouple contact TEMP−, a PZE contact PZE−, and an LED contact LED/PD− (part of the array 156 of FIG. 1), formed by contact 414 coupling the LED/PD portion of the PPMG sensor component with the joint 420, to save a wire in the harness 402.

Remaining contacts in the wiring harness 402 may include other contacts of the array 156, such as LED+ and PD+, and another PZE contact PZE+. Importantly, the contact 412 may further comprise a voltage contact V+ corresponding to contact 150 V+ of FIG. 3.

The interconnection of sensor 300 may be provided via the wiring harness 404 in a similar way. As shown, contact 350 extending from the bottom electrode 330 of the sensor 300 may include contact V−, which in combination with corresponding contact V+ of sensor 100 may provide a voltage probe 430, for reading voltage from the electrodes 130, 330, or for inducing voltage into electrodes 130, 330.

Figure 5:
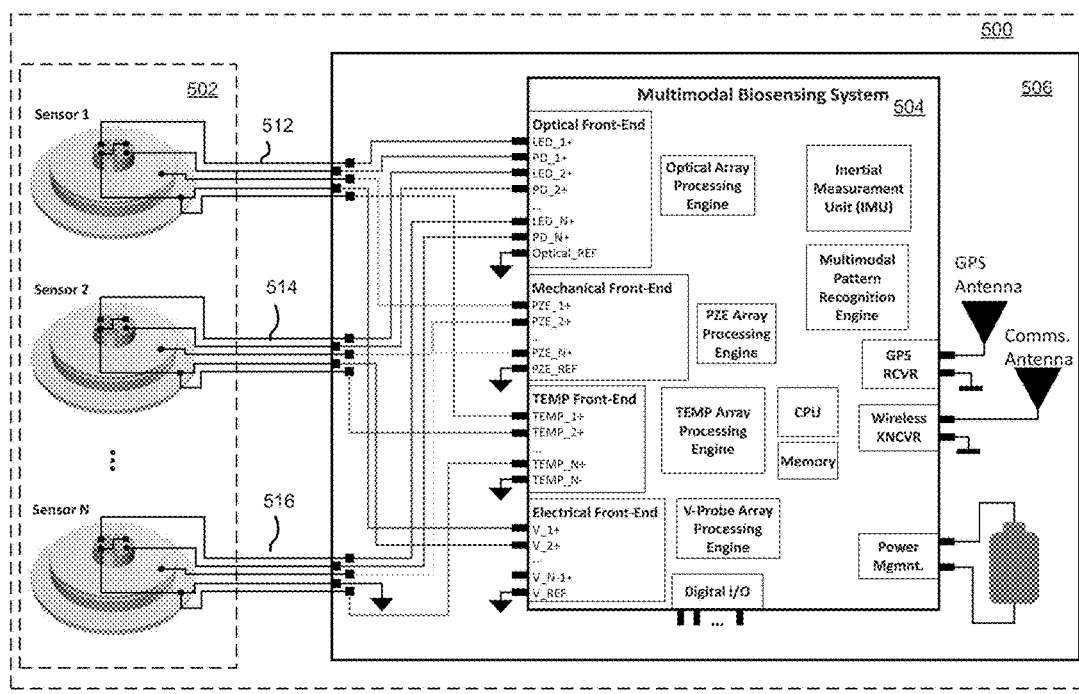
FIG. 5 is a block diagram illustrating an example apparatus for measurements of a user's physiological context, configured with a multi-modal sensing system, in accordance with some embodiments.

FIG. 5 is a block diagram illustrating an example apparatus for measurements of a user's physiological context, configured with a multi-modal sensing system, in accordance with some embodiments. In embodiments, the apparatus may comprise a wearable device and may include a sensor array coupled with a processing block as briefly described in reference to FIG. 4.

As shown, the apparatus 500 may include a sensor array 502, which may include sensors 1, 2, . . . , N configured as described in reference to FIGS. 1-4. The sensors 1, 2, . . . , N of the array 502 may be coupled with a processing block 504 (disposed on a PCB 506) via respective interconnects 512, 514, . . . , 516. The processing block 504 may comprise a multi-modal sensing system configured to receive and process readings of the user's physiological context from the sensor array 502.

More specifically, respective PPMG sensor components of the sensors in the array 502 may be coupled with an optical front end block of the processing block 504. Respective PZE sensor components may be coupled with a mechanical front end of the processing block 504. Respective thermocouples may be coupled with a temperature front end of the processing block 504. Voltage contacts may comprise respective contacts V+ extending from the bottom electrodes of each sensor in the array, except one contact of one sensor (e.g., sensor N in FIG. 5), which may serve as reference (ground) V_REF for all other voltage contacts. Voltage contacts may be coupled with an electrical front end of the processing block 504.

Accordingly, the processing block 504 may integrate the front end blocks required to condition the optical, electrical, mechanical, and temperature based signals generated by the sensor array as described above, and provide the signals to array processing engines for processing. The respective array processing engines may be configured to process the signals received from the sensor array and provide the processed signals to a pattern recognition engine for further interpretation.

Additionally, the processing block 504 may include an Inertial Measurement Unit (IMU) for apparatus 500 (e.g., wearable device) position tracking, recognition engines for efficient and multi-modal pattern classification, a Global Positioning System (GPS) receiver for location tracking, wired and wireless interfaces, and the required power management circuitry. The processing block may include a processor to operate the processing block 504, and a memory to store instructions for block 504 operation, as well as the results of the analysis and processing of data received from the sensor array.

The processor may include, for example, one or more processors situated in separate components, or alternatively one or more processing cores embodied in a component (e.g., in a System-on-a-Chip (SoC) configuration), and any processor-related support circuitry (e.g., bridging interfaces, etc.). Example processors may include, but are not limited to, various microprocessors including those in the Pentium®, Xeon®, Itanium®, Celeron®, Atom®, Quark®, Core® product families, or the like.

Examples of support circuitry may include host side or input/output (I/O) side chipsets (also known as northbridge and southbridge chipsets/components) to provide an interface through which the processor may interact with other system components that may be operating at different speeds, on different buses, etc. in the apparatus 500. Some or all of the functionality commonly associated with the support circuitry may also be included in the same physical package as the processor.

The memory may comprise random access memory (RAM) or read-only memory (ROM) in a fixed or removable format. RAM may include volatile memory configured to hold information during the operation of the apparatus 500 such as, for example, static RAM (SRAM) or Dynamic RAM (DRAM). ROM may include non-volatile (NV) memory circuitry configured based on basic input/output system (BIOS), Unified Extensible Firmware Interface (UEFI), etc. to provide instructions when the apparatus 500 is activated, programmable memories such as electronic programmable ROMs (erasable programmable read-only memory), Flash, etc. Other fixed/removable memory may include, but is not limited to, electronic memories such as solid state flash memory, removable memory cards or sticks, etc.

The wireless communication block may be communicatively coupled with an external device (not shown) and may include one or more radios capable of transmitting and receiving signals using various suitable wireless communications techniques. Such techniques may involve communications across one or more wireless networks. Some example wireless networks include (but are not limited to) wireless local area networks (WLANs), wireless personal area networks (WPANs), wireless metropolitan area network (WMANs), cellular networks, and satellite networks. In communicating across such networks, the communication block may operate in accordance with one or more applicable standards in any version. To this end, the communication block may include, for instance, hardware, circuits, software, or any combination thereof that allows communication with external computer systems.

In some specific non-limiting examples, the communication block may comport with the Institute of Electrical and Electronics Engineers (IEEE) 802.11 standard (e.g., Wi-Fi), a Bluetooth®, ZigBee®, near-field communication, or any other suitable wireless communication standard. In addition, the communication block may comport with cellular standards such as 3G (e.g., Evolution-Data Optimized (EV-DO), Wideband Code Division Multiple Access (W-CDMA)) and/or 4G wireless standards (e.g., High Speed Packet Access (HSPA), Worldwide Interoperability for Microwave Access (WIMAX), Long-Term Evolution (LTE)).

The processing block 504 may further include a power management block configured to provide power supply to the components of the apparatus 500. In some embodiments, the power management block may be configured to power on the apparatus 500 continuously or periodically, in order to save battery power. The power management block may include internal power sources (e.g., battery, fuel cell, etc.) and/or external power sources (e.g., power grid, electromechanical or solar generator, external fuel cell, etc.) and related circuitry configured to supply apparatus 500 with the power needed to operate.

The processing block 504 may include other components that may be necessary for functioning of the apparatus 500. Other components may include, for example, hardware and/or software to allow users to interact with the apparatus 500 such as, for example, various input mechanisms (e.g., microphones, switches, buttons, knobs, keyboards, speakers, touch-sensitive surfaces, one or more sensors configured to capture images and/or sense proximity, distance, motion, gestures, orientation, biometric data, etc.) and various output mechanisms (e.g., speakers, displays, lighted/flashing indicators, electromechanical components for vibration, motion, etc.). For example the processing block 504 may include a digital input/output (I/O) port to provide communication capabilities with external devices.

Figure 6:
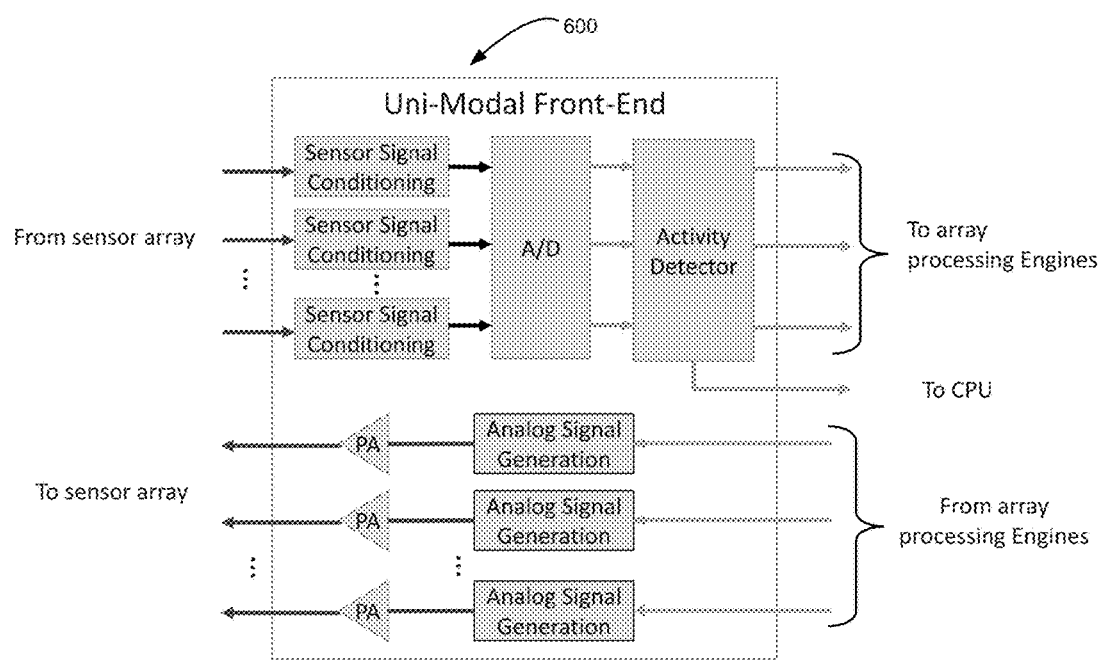
FIG. 6 is a block diagram of a uni-modal front end block of the example multi-modal sensing system described in reference to FIG. 5, in accordance with some embodiments.
Figure 7:
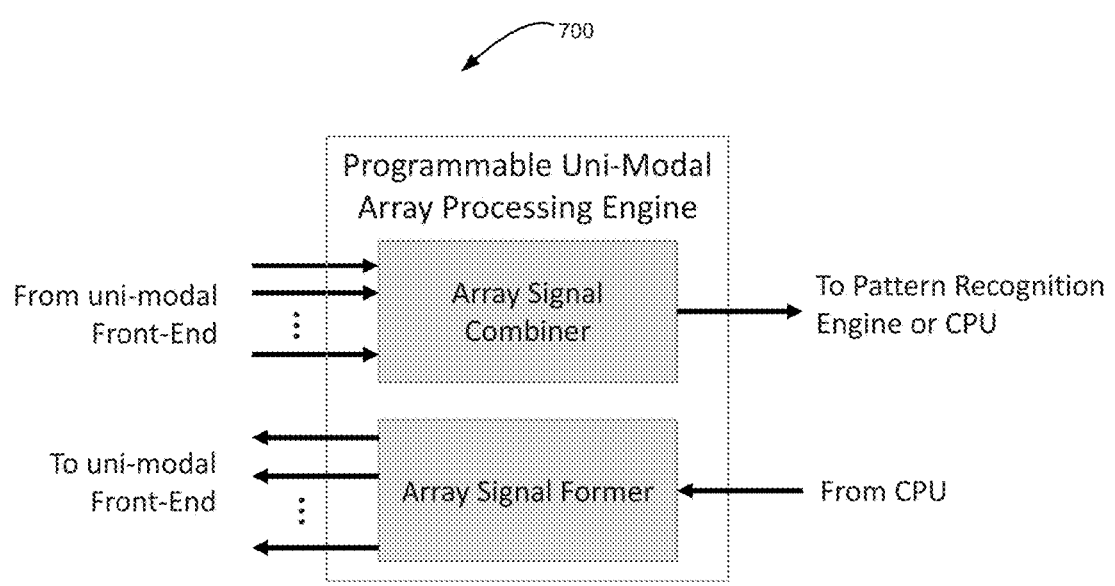
FIG. 7 is a block diagram of a uni-modal array processing block of the example multi-modal sensing system described in reference to FIG. 5, in accordance with some embodiments.
Figure 8:
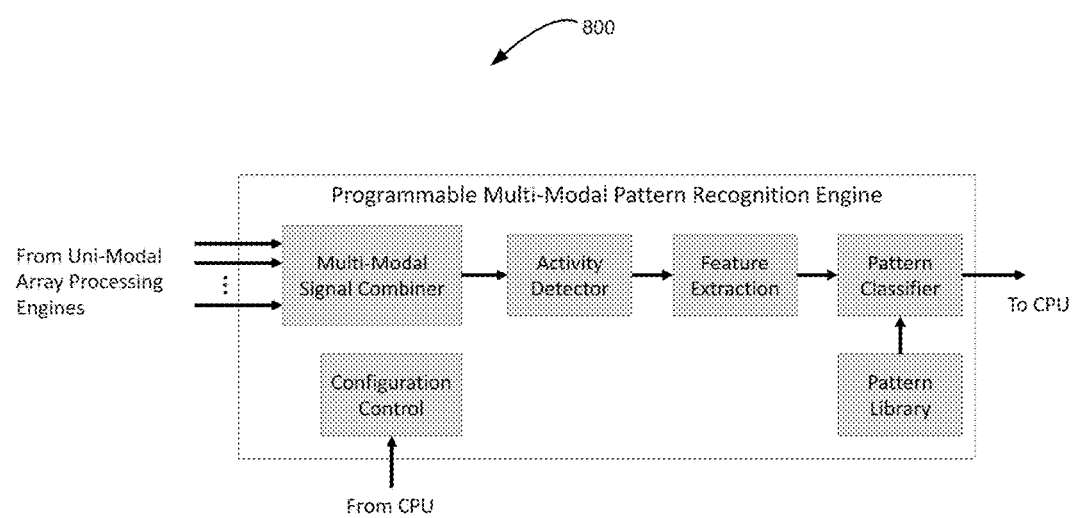
FIG. 8 is a block diagram of a multi-modal pattern recognition block of the example multi-modal sensing system described in reference to FIG. 5, in accordance with some embodiments.

Some of the blocks of the multi-modal sensing system comprising the processing block 504 are described in detail in reference to FIGS. 6-8.

FIG. 6 is a block diagram of a uni-modal front end block of the example multi-modal sensing system described in reference to FIG. 5, in accordance with some embodiments. The term "uni-modal" is used herein to denote any of the different modes of the user's physiological context measurements that may be provided by the sensor array, such as electrical, mechanical, optical, or temperature as described above. Accordingly, the description below may apply to any of the front end blocks of the processing block 504 of FIG. 5, such as electrical front end, optical front end, mechanical front end, or temperature front end. In other words, all front end blocks of the processing block 504 may have similar features as those described in reference to the uni-modal front end block 600 of FIG. 6.

The uni-modal front end block 600 may provide for conditioning and digitizing the analog signals received from the sensors (e.g., N total sensors) in the sensor array 502. As such, each circuitry set of a front end block may be different for each kind of signal (e.g., optical, mechanical, temperature and electrical). However, there may be N replicas per type of signal provided by the sensors. Once the analog signals are conditioned at sensor signal conditioning sub-block and digitized at analog-to-digital converter (ADC), an activity detector block may provide the digitized signals to a respective array processing engine.

Additionally, for any type of signal except the thermal, a signal generating circuitry may be provided. For example, the optical front end block may include the analog signal generation circuitry to generate (synthesize) an analog signal to the LED besides the signal conditioning circuitry that may condition the signal received by the PD of the PPMG sensor component of a sensor. Similarly, analog signal generation circuitry to inject a voltage into the piezoelectric elements in order to induce a vibration sensation may be included in the mechanical front end block.

FIG. 7 is a block diagram of a uni-modal array processing engine (block) of the example multi-modal sensing system described in reference to FIG. 5, in accordance with some embodiments. The description below may apply to any of the array processing engines (blocks) of the processing block 504 of FIG. 5.

The array processing block 700 may be configured to perform two specialized functions. First, the array processing block 700 may combine the digitized signals from the sensors of the same type into a unique signal, at an array signal combiner. The combined signal may contain the information from all of the sensors in the array. More specifically, the properties of a combined signal may be compared to the properties of some other signals that may be stored and accessible by the processing block 504. Specifically, a combined signal is provided per signal type, that is, there may be four independent combined signals corresponding to electrical, mechanical, optical and temperature sensing modes, according to four uni-modal array processing engines (blocks) present in the apparatus 500. In other words, one combined signal is generated per array processing engine (block). More generally, signals of the same type of sensing (electrical, mechanical, optical, or temperature) are combined into one signal. There may be a training phase of the array processing block, in which the user may record the reference signals. For example, for hand gesture recognition, the user may perform each gesture a number of times and save the corresponding signals provided by the sensors of the sensor array, to be used as a reference. When the user performs a gesture, the system may combine the signals and compare the characteristics of a yet unknown signal to the characteristics of the reference signals. If the characteristics match with a desired margin of error, the signal may be classified as a gesture.

The term "combined signal" may not only mean a simple combination of signals, but may also imply the use of more advanced algorithms, for example, neural networks, to produce a combination of the signals.

The second function of the array processing block 700 may be the generation of digital array signals at an array signal former that may feed the analog signal generation block at a respective front end block (see FIG. 6). This function may be programmable, so that the user may decide the specific signal combination method depending on the application. For example, the analog signals sent back to the sensor for user stimulation or for driving LED (as described above) may be related and may depend from each other.

For example, the signal amplitudes and delays may be relative to one another; in other words, the signals may have the same or similar shape, but may be scaled in amplitude and displaced in time with respect to one another. These relations may be determined in a digital domain by the array signal former. The determined features (e.g., amplitude, shape, time delay, etc.) may be sent to the analog signal generation blocks at respective front end blocks as digital commences. The analog signal generation blocks may react to these commands to generate corresponding analog signals.

The inter-relation of the signals provided to the sensors may depend on a desired result. For example, to conduct mechanical vibration wireless communication, the ultrasonic mechanical vibrations at each transmitting PZE sensor component may be related in a way that may allow focusing the signal in a certain direction. The same may occur at the receiving signals. Depending on how the signals may be combined, the signals coming from different spatial directions may be favored. For example, in ultrasonic imaging, it may be beneficial to "focus" on the signals coming from a particular direction. For example, if a pad of sensors is placed at the user's abdomen, a sensed signal combination may allow for "listening" sounds reflecting back from an organ of interest. The same applies to the signals that may be injected into the user's body. The sound or vibrations may be directed to propagate to a certain direction, e.g., the stomach, the liver, the bladder, etc. These types of signal combinations may be typical for mechanical vibration applications (like sound source location or ultrasonic imaging) and in electromagnetic signal applications (wireless communications, imaging, radio location, etc).

Array processing engines (blocks) may be realized by hardware circuitry or software algorithms within a processor. Hardware implementations may lead to more efficient power consumption and performance of the system.

FIG. 8 is a block diagram of a multi-modal pattern recognition engine (block) of the example multi-modal sensing system described in reference to FIG. 5, in accordance with some embodiments.

The multi-modal pattern recognition block 800 may receive the signals from the individual uni-modal array processing blocks, for example, from at least two of them, or from all of them. If receiving only one type of signal, then this block may become a typical pattern recognition block. The multi-modal pattern recognition block 800 may analyze the received signals for the detection of pre-defined patterns. Since many pattern recognition approaches are available, the multi-modal pattern recognition block 800 may be programmable to allow the user to target different applications. The multi-modal signal combiner of the pattern recognition block may combine different array signals into a new combined, single multi-modal signal. An activity detector block may determine whether a probable valid activity is expected in the signal. The activity detector may be interchanged with the one shown in FIG. 6 or added as an extra-layer of activity detection. The feature extraction and pattern classifier blocks may determine whether the multi-modal signal corresponds to a valid pattern stored in the pattern library. The configuration control block may enable the programmability of each of the other blocks. If information about a single type of signal is desired, then multi-modal pattern recognition may be bypassed and configured to uni-modal pattern recognition. In another example, the combined signal may provide information about an event of interest with respect to user's activity or health. For example, temperature data, skin conductivity data, EEG, pulse rate data, and ECG may be interpreted from the combined signal to determine the user's stress level.

The multi-modal pattern recognition block 800 may be realized as software, hardware, or a combination thereof. Hardware implementation may lead to power and performance efficient embodiments.

The advantages of the wearable device comprising the multi-modal sensing system and the sensor array described above a may include an increased range of applications. For example, the wearable device may be used to provide measurements of the user's physiological context that may be used to determine the user's brain and body activity, gestures and speech recognition, vital signs monitoring, full-body health monitoring, and the like.

Figure 9:
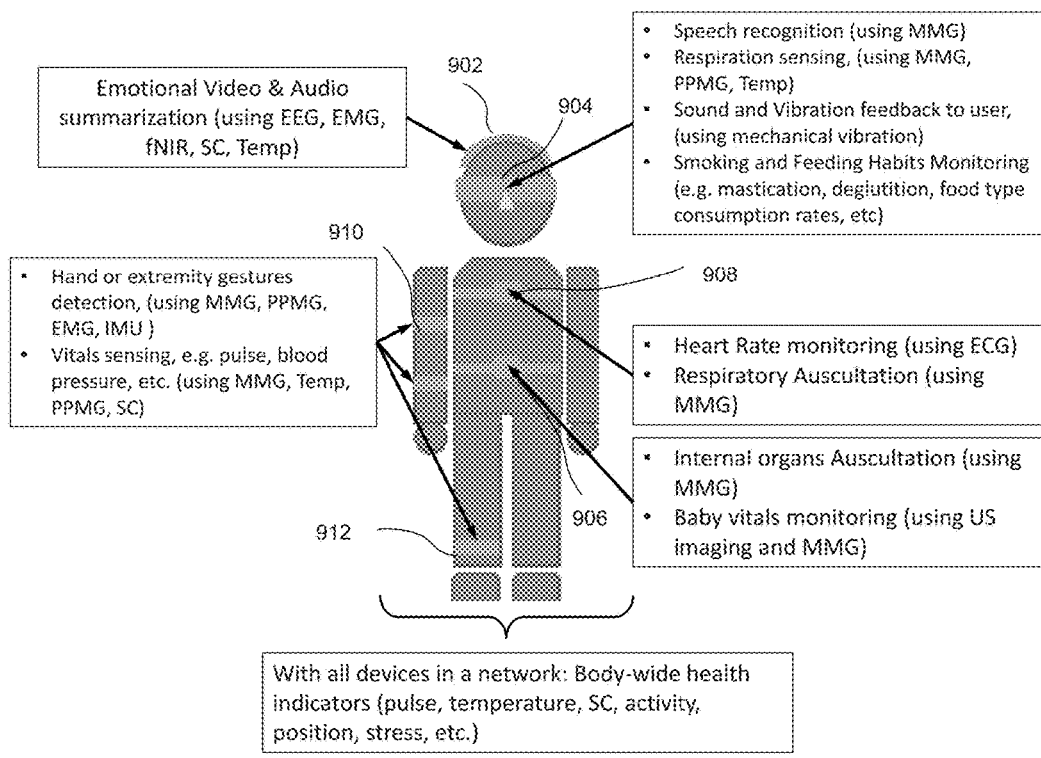
FIG. 9 is a schematic diagram illustrating example applications of a wearable device configured with the multi-modal sensing system, in accordance with some embodiments.

FIG. 9 is a schematic diagram illustrating example applications of a wearable device configured with the multi-modal sensing system, in accordance with some embodiments.

As shown, the example applications may include emotional video and audio summarization, based on EEG, EMG, fNIR, skin conductivity (SC), and temperature data provided by the sensing system. The wearable device may be implemented as a portion of a headwear 902 of the user, as shown.

Further example applications may include speech recognition (using MMG), respiration sensing, (using MMG, PPMG, and temperature data), sound and vibration feedback to the user, (using mechanical vibration) or smoking and feeding habits monitoring (e.g. mastication, deglutition, food type consumption rates, etc). The wearable device may be implemented as a portion of eyewear 904 of the user, as shown.

Further example applications may include heart rate monitoring (using ECG) and respiratory auscultation (using MMG), and internal organs auscultation (using MMG), baby vitals monitoring (using imaging and MMG). The wearable device may be implemented as a portion of clothing of the user, such as a belt 906 or attachment to a coat 908, as shown.

Further example applications may include hand or extremity gestures detection, (using MMG, PPMG, EMG, IMU) vitals sensing, e.g. pulse, blood pressure, etc. (using MMG, temperature, PPMG, SC). The wearable device may be implemented as a portion of clothing of the user, such as arm-band 910 or knee-band 912, as shown.

In summary, the wearable device configured with the multi-modal sensing system may provide body-wide health indicators, such as pulse, temperature, activity, position, stress, and the like. Examples of wearable devices configured with the multi-modal sensing system used for applications described in reference to FIG. 9 may include a wrist device, finger device, smart glasses, smart bracelets, smart fitness bands, ring device, neck-pendant device, belt-clip device, arm-band device, shoe devices, clothing devices, and other wearable devices.

Figure 10:
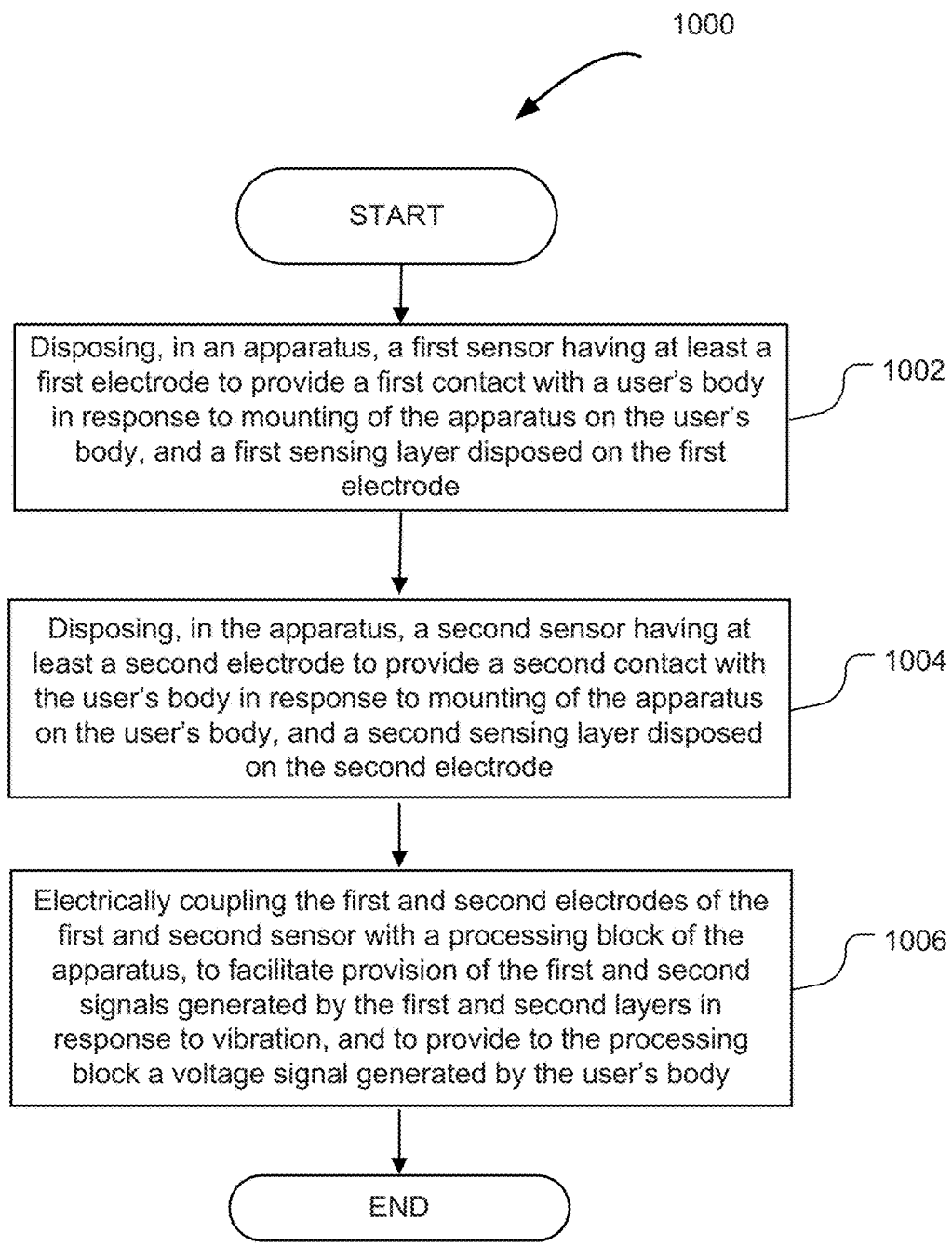
FIG. 10 is an example process flow diagram for fabricating a wearable device configured with the multi-modal sensing system for providing measurements of the user's physiological context, in accordance with some embodiments.

FIG. 10 is an example process flow diagram for fabricating a wearable device configured with the multi-modal sensing system for providing measurements of the user's physiological context, in accordance with some embodiments. The process 1000 may comport with some of the apparatus embodiments described in reference to FIGS. 1-9. For example, the apparatus may comprise an apparatus 500 with sensor array 502 and processing block 504 of FIG. 5. In alternate embodiments, the process 1000 may be practiced with more or fewer operations, or a different order of the operations.

The process 1000 may begin at block 1002 and include disposing, in an apparatus, a first sensor having at least a first electrode to provide a first contact with a user's body in response to mounting of the apparatus on the user's body, and a first sensing layer disposed on the first electrode. The first sensor may comprise sensor 100 of FIGS. 1 and 3-4.

At block 1004, the process 1000 may include disposing, in the apparatus, a second sensor having at least a second electrode to provide a second contact with the user's body in response to mounting of the apparatus on the user's body, and a second sensing layer disposed on the second electrode. The second sensor may comprise sensor 300 of FIGS. 3-4.

The first and second sensors may include respective third and fourth electrodes, wherein the first and second sensing layers (e.g. PZE material) may be sandwiched between the first and third electrodes and the second and fourth electrodes respectively.

The process 1000 may further include disposing a processing block in the apparatus, for example, prior to disposing first and second sensors in the apparatus.

At block 1006, the process 1000 may include electrically coupling the first and second electrodes of the first and second sensors with the processing block disposed in the apparatus, to facilitate provision of the first and second signals generated by the first and second layers in response to vibration, and to provide to the processing block a voltage signal generated by the user's body, to perform measurements of a user's physiological context. The voltage signal may comprise a difference between respective voltages on the first and second electrodes of the first and second sensors.

The process 1000 may further include electrically coupling the third and fourth electrodes with the processing block, to provide the first signal via the first and third electrodes, and the second signal via the second and fourth electrodes, to the processing block.

The following paragraphs describe examples of various embodiments.

Example 1 may be an apparatus for measurements of a user's physiological context, comprising: a processing block and a sensor array coupled with the processing block, wherein the sensor array includes: a first sensor, having at least a first electrode to provide a first contact with a user's body in response to mounting of the apparatus on the user's body, wherein the first electrode is coupled with the processing block, to facilitate a provision of a first signal to be generated by the first sensor to the processing block in response to the first contact; and a second sensor, having at least a second electrode to provide a second contact with the user's body in response to mounting of the apparatus on the user's body, wherein the second electrode is coupled with the processing block, to facilitate a provision of a second signal to be generated by the second sensor to the processing block in response to the second contact, wherein the processing block is to perform measurements of a user's physiological context based at least in part on a voltage signal to be generated by the user's body and provided by the first and second electrodes in response to the first and second contacts of the user's body with the first and second sensors, and on the first and second signals of the first and second sensors.

Example 2 may include the subject matter of Example 1, wherein the processing block to perform measurements of a user's physiological context includes the processing block to process the voltage signal received from the first and second electrodes, to obtain at least one of: electrocardiogram, ECG, data, electromyogram, EMG, data, or electroencephalogram, EEG, data.

Example 3 may include the subject matter of Example 1, wherein the first sensor further includes a first sensing layer disposed on the first electrode, and wherein the second sensor further includes a second sensing layer disposed on the second electrode, wherein the first and second sensing layers are to generate the first and second signals in response to vibration of the user's body.

Example 4 may include the subject matter of Example 3, wherein the first and second sensing layers comprise a piezoelectric material.

Example 5 may include the subject matter of Example 3, wherein the first sensor further includes a third electrode disposed on top of the first sensing layer, wherein the third electrode is coupled with the processing block, wherein the first signal is to be provided via the first and third electrodes of the first sensor.

Example 6 may include the subject matter of Example 5, wherein the second sensor further includes a fourth electrode disposed on top of the second sensing layer, wherein the fourth electrode is coupled with the processing block, wherein the second signal to be generated by the second sensing layer is to be provided via the second and fourth electrodes of the second sensor.

Example 7 may include the subject matter of Example 6, wherein the first electrode is coupled with the processing block over a first electrical contact, wherein the second electrode is coupled with the processing block over a second electrical contact, wherein the third electrode is coupled with the processing block over a third electrical contact, wherein the fourth electrode is coupled with the processing block over a fourth electrical contact, wherein the first electrode is further coupled with the processing block over a fifth electrical contact, wherein the first and fifth electrical contacts comprise a first thermocouple, and wherein the second electrode is further coupled with the processing block over a sixth electrical contact, wherein the second and sixth electrical contacts comprise a second thermocouple, to provide respectively third and fourth signals indicative of a temperature of the user's body to the processing block.

Example 8 may include the subject matter of Example 7, wherein the first sensor further includes a first optical sensing device disposed in the first sensor to provide a first proximity to or a third contact with the user's body in response to mounting of the apparatus on the user's body, wherein the second sensor further includes a second optical sensing device disposed in the second sensor to provide a second proximity to or a fourth contact with the user's body in response to mounting of the apparatus on the user's body, wherein the first and second optical sensing devices are coupled with the processing block, to provide respectively fifth and sixth signals that are indicative of photoplethysmography, PPMG, of the user's body to the processing block.

Example 9 may include the subject matter of Example 8, wherein the processing block includes: a front end block, to receive, pre-process and digitize the first, second, third, fourth, fifth, and sixth signals, and the voltage signal generated by the user's body; an array processing block coupled with the front end block, to receive the digitized first, second, third, and fourth signals, and the voltage signal from the front end block, and to integrate the received signals into a combined signal that includes information provided by the first and second sensors; and a pattern recognition block coupled with the array processing block, to receive and analyze the combined signal, based at least in part on pre-defined signal patterns.

Example 10 may include the subject matter of Example 1, wherein the processing block includes an inertial measurement unit, IMU, to perform position tracking of the user's body, and a global positioning system, GPS, unit to perform location tracking of the apparatus.

Example 11 may include the subject matter of Example 1, wherein the processing block is to generate and induce voltage into the user's body via the first and second electrodes of the first and second sensors, to perform further measurements of the user's physiological context or to perform therapeutic treatment of the user.

Example 12 may include the subject matter of any Examples 1 to 11, wherein the apparatus comprises a wearable device.

Example 13 may be a method for providing an apparatus for measurements of a user's physiological context, comprising: disposing, in an apparatus, a first sensor having at least a first electrode to provide a first contact with a user's body in response to mounting of the apparatus on the user's body, and a first sensing layer disposed on the first electrode; disposing, in the apparatus, a second sensor having at least a second electrode to provide a second contact with the user's body in response to mounting of the apparatus on the user's body, and a second sensing layer disposed on the second electrode; and electrically coupling the first and second electrodes of the first and second sensors with a processing block of the apparatus, to facilitate provision of first and second signals generated by the first and second layers in response to vibration, and to provide to the processing block a voltage signal generated by the user's body, to perform measurements of a user's physiological context, wherein the voltage signal comprises a difference between respective voltages on the first and second electrodes of the first and second sensors.

Example 14 may include the subject matter of Example 13, wherein the apparatus comprises a wearable device.

Example 15 may include the subject matter of Example 13, wherein the first and second sensors include respective third and fourth electrodes, wherein the first and second sensing layers are sandwiched between the first and third electrodes and the second and fourth electrodes respectively, wherein the first and second sensing layers comprise a piezoelectric material, wherein the method further comprises: electrically coupling the third and fourth electrodes with the processing block, to provide the first signal via the first and third electrodes, and the second signal via the second and fourth electrodes, to the processing block.

Example 16 may include the subject matter of any Examples 13 to 15, further comprising: disposing the processing block in the apparatus.

Example 17 may be an apparatus for measurements of a user's physiological context, comprising: a processing block; and first and second piezoelectric sensors coupled with the processing block, wherein the first and second sensors include respectively first and second electrodes to provide contact with a user's body in response to mounting of the apparatus on the user's body, wherein the processing block is to perform measurements of a user's physiological context during the contact of the user's body with the first and second electrodes, based at least in part on a voltage signal generated by the user's body and provided to the processing block via the first and second electrodes.

Example 18 may include the subject matter of Example 17, wherein the processing block is to further perform measurements of the user's physiological context based on signals indicative of the user's body vibration provided by the first and second piezoelectric sensors.

Example 19 may include the subject matter of Example 18, wherein the first and second piezoelectric sensors include first and second thermocouples, to provide signals indicative of a temperature of the user's body, and further include first and second optical sensing devices, to provide signals indicative of photoplethysmography, PPMG, of the user's body to the processing block, wherein the processing block is to further perform measurements of a user's physiological context based at least in part on the signals indicative of a temperature of the user's body and the signals indicative of PPMG of the user's body.

Example 20 may include the subject matter of Example 19, wherein the processing block to perform measurements of the user's physiological context includes to: integrate the voltage signal, the signals indicative of the user's body vibration, the signals indicative of a temperature of the user's body and the signals indicative of PPMG of the user's body into a combined signal; and identify data indicative of the user's physiological context based at least in part on pre-determined signal patterns.

Example 21 may include the subject matter of any Examples 17 to 20, wherein the processing block is to process the voltage signal to obtain at least one of: electrocardiogram, ECG, data, electromyogram, EMG, data, or electroencephalogram, EEG, data.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. An apparatus, comprising: a sensor array to be coupled with a processing block, wherein the sensor array includes:
a first sensor, having: a first electrode to provide a first contact with a user's body, wherein the first electrode is to be coupled with the processing block with a first electrical contact; a first sensing layer comprising piezoelectric material and disposed on top of the first electrode; and a second electrode disposed on top of the first sensing layer, wherein the second electrode is to be coupled with the processing block with a second electrical contact, wherein the first and second electrical contacts are to provide first readings of vibrations produced by the user's body and sensed by the first sensing layer; and
a second sensor, having: a third electrode to provide a second contact with the user's body, wherein the second electrode is to be coupled with the processing block with a third electrical contact; a second sensing layer comprising the piezoelectric material and disposed on top of the third electrode, and a fourth electrode disposed on top of the second sensing layer, wherein the fourth electrode is to be coupled with the processing block with a fourth electrical contact, wherein the third and fourth electrical contacts are to provide second readings of vibrations produced by the user's body and sensed by the second sensing layer, wherein the first electrode of the first sensor and the third electrode of the second sensor are to sense a voltage of the user's body, and to provide the sensed voltage to the processing block via the first electrical contact of the first sensor and the third electrical contact of the second sensor, wherein one of the first electrode with the first contact of the first sensor and the third electrode with the third electrical contact of the second sensor serves as reference voltage for another one of the first electrode with the first contact of the first sensor and the third electrode with the third electrical contact of the second sensor,
wherein the processing block is to perform first measurements of a user's physiological context, based at least in part on the sensed voltage provided by the first and third electrodes in response to the first and second contacts of the user's body with the first and second sensors, and generate a first output that includes at least electrocardiogram (ECG), from the first measurements; and perform second measurements of the user's physiological context, based at least in part on the first and second readings of vibrations produced by the user's body, and generate a second output indicative of the user's body activity.

2. The apparatus of claim 1, wherein the first electrode is further coupled with the processing block over a fifth electrical contact, wherein the first and fifth electrical contacts comprise a first thermocouple, and
wherein the second electrode is further coupled with the processing block over a sixth electrical contact, wherein the second and sixth electrical contacts comprise a second thermocouple, to provide respective signals indicative of a temperature of the user's body to the processing block.

3. The apparatus of claim 2, wherein the first sensor further includes a first optical sensing device disposed in the first sensor to provide a first proximity to or a third contact with the user's body in response to mounting of the apparatus on the user's body,
wherein the second sensor further includes a second optical sensing device disposed in the second sensor to provide a second proximity to or a fourth contact with the user's body in response to mounting of the apparatus on the user's body,
wherein the first and second optical sensing devices are coupled with the processing block, to provide respective signals that are indicative of photoplethysmography, PPMG, of the user's body to the processing block.

4. The apparatus of claim 3, wherein the processing block includes:
a front end block, to receive, pre-process and digitize signals provided by the first and second sensors;
an array processing block coupled with the front end block, to receive the digitized signals, and to integrate the received digitized signals into a combined signal; and
a pattern recognition block coupled with the array processing block, to receive and analyze the combined signal, based at least in part on pre-defined signal patterns.

5. The apparatus of claim 1, wherein the first output further includes at least one of: electromyogram, EMG, or electroencephalogram, EEG.

6. The apparatus of claim 1, wherein the processing block includes an inertial measurement unit, IMU, to perform position tracking of the user's body, and a global positioning system, GPS, unit to perform location tracking of the apparatus.

7. The apparatus of claim 1, wherein the processing block is to generate and induce voltage into the user's body via the first and second electrodes of the first and second sensors, to perform further measurements of the user's physiological context or to perform therapeutic treatment of the user.

8. The apparatus of claim 1, wherein the apparatus comprises a wearable device.

9. An apparatus, comprising:
a processing block; and
first and second piezoelectric sensors coupled with the processing block, wherein the first sensor includes:
a first electrode to provide a first contact with a user's body, wherein the first electrode is coupled with the processing block with a first electrical contact; a first sensing layer comprising piezoelectric material and disposed on top of the first electrode; and a second electrode disposed on top of the first sensing layer, wherein the second electrode is coupled with the processing block with a second electrical contact, wherein the first and second electrical contacts provide first readings of vibrations produced by the user's body and sensed by the first sensing layer; and wherein the second sensor includes:
a third electrode to provide a second contact with the user's body, wherein the second electrode is to be coupled with the processing block with a third electrical contact; a second sensing layer comprising the piezoelectric material and disposed on top of the third electrode, and a fourth electrode disposed on top of the second sensing layer, wherein the fourth electrode is to be coupled with the processing block with a fourth electrical contact, wherein the third and fourth electrical contacts are to provide second readings of vibrations produced by the user's body and sensed by the second sensing layer, wherein one of the first electrode with the first contact of the first sensor and the third electrode with the third electrical contact of the second sensor serves as reference voltage for another one of the first electrode with the first contact of the first sensor and the third electrode with the third electrical contact of the second sensor,
wherein the processing block is to:
perform first measurements of a user's physiological context during the first and second contacts of the user's body with the first and third electrodes, based at least in part on the sensed voltage provided by the first and third electrodes in response to the first and second contacts of the user's body with the first and second sensors, and generate a first output that includes at least electrocardiogram (ECG), from the first measurements; and
perform second measurements of the user's physiological context, based at least in part on the first and second readings of vibrations produced by the user's body, and generate a second output indicative of the user's body activity.

10. The apparatus of claim 9, wherein the first and second piezoelectric sensors include first and second thermocouples, to provide signals indicative of a temperature of the user's body, and further include first and second optical sensing devices, to provide signals indicative of photoplethysmogrpaphy PPMG, of the user's body to the processing block, wherein the processing block is to further perform measurements of the user's physiological context based at least in part on the signals indicative of a temperature of the user's body and the signals indicative of PPMG of the user's body.

11. The apparatus of claim 10, wherein the processing block is to:
integrate the voltage, signals indicative of the user's body vibrations, the signals indicative of a temperature of the user's body and the signals indicative of PPMG of the user's body into a combined signal; and
generate data indicative of the user's physiological context based at least in part on pre-determined signal patterns.

12. The apparatus of claim 9, wherein the first output further includes at least one of: electromyogram, EMG, or electroencephalogram, EEG.

13. A method, comprising:
disposing, in an apparatus, a first sensor having: a first electrode to provide a first contact with a user's body; a first sensing layer comprising piezoelectric material and disposed on top of the first electrode; and a second electrode disposed on top of the first sensing layer;
disposing, in the apparatus, a second sensor having: a third electrode to provide a second contact with the user's body; a second sensing layer comprising the piezoelectric material and disposed on top of the second electrode; and a fourth electrode disposed on top of the second sensing layer;

electrically coupling the first and second electrodes of the first sensor with a processing block of the apparatus, via respective first and second electrical contacts, to facilitate provision of first readings of vibrations produced by the user's body and sensed by the first sensing layer; and electrically coupling the third and fourth electrodes of the second sensor with the processing block, via respective third and fourth electrical contacts, to provide second readings of vibrations produced by the user's body and sensed by the second sensing layer, wherein the electrical coupling to the processing block of the first electrode via the first electrical contact and the third electrode via the third electrical contact is to provide to the processing block a voltage signal generated by the user's body and sensed by the first and third electrodes of the first and second sensors, and to further provide for one of the first electrode with the first contact of the first sensor and the third electrode with the third electrical contact of the second sensor serving as reference voltage for another one of the first electrode with the first contact of the first sensor and the third electrode with the third electrical contact of the second sensor.

14. The method of claim 13, wherein the apparatus comprises a wearable device.

15. The method of claim 13, further comprising: disposing the processing block in the apparatus.

* * * * *